United States Patent

Fujioka et al.

[11] Patent Number: 5,827,257
[45] Date of Patent: Oct. 27, 1998

[54] URINE-ABSORBENT BAG

[75] Inventors: Yoshihisa Fujioka, Kagawa-ken; Norihiko Ishikawa, Ehime-ken, both of Japan

[73] Assignee: Uni-Charm Corporation, Ehime-ken, Japan

[21] Appl. No.: 787,478

[22] Filed: Jan. 22, 1997

[30] Foreign Application Priority Data

Jan. 31, 1996 [JP] Japan ................................ 8-015993

[51] Int. Cl.⁶ .............................. A61F 13/15; A61F 5/44
[52] U.S. Cl. ...................... 604/385.1; 604/349; 604/352
[58] Field of Search .................................. 604/349–352, 604/380, 379, 385.1

[56] References Cited

U.S. PATENT DOCUMENTS 4,590,931  5/1986  Kidwell, Jr. .
5,735,837  4/1998  Ishikawa .................................. 604/352

FOREIGN PATENT DOCUMENTS

2701389A1   8/1994  France .
7-124190    5/1995  Japan .
WO 86/01378 3/1986  WIPO .
WO 92/15269 9/1992  WIPO .

*Primary Examiner*—Robert A. Clarke
*Attorney, Agent, or Firm*—Lowe Hauptman Gopstein Gilman & Berner

[57] ABSTRACT

A urine-absorbent bag having front and rear sections for covering of the user's penis and an opening for insertion of the user's penis into the bag, the bag being composed of a liquid-permeable inner sheet, a liquid-impermeable outer sheet and a liquid-absorbent core disposed therebetween, the core being formed with grooves in predetermined directions to thereby deform the bag following a shape of the user's penis and allow an absorbing capacity of the core to be fully utilized.

8 Claims, 3 Drawing Sheets

URINE-ABSORBENT BAG

BACKGROUND OF THE INVENTION

The present invention relates gerenally to a urine-absorbent bag and more particularly to a urine-absorbent bag for male patients suffering from incontinence including bedridden male patients and the like.

Japanese Laid-Open Patent Application No. Hei7-124190 discloses an example of a urine-absorbent bag formed by bonding a top layer to a back layer along both side edges and a bottom edge thereof so as to define at a top thereof an opening for insertion of the user's penis. The top layer comprises a nonwoven fabric and the back layer comprises a stretchable nonwoven fabric and the back layer comprises a stretchable nonwoven fabric defining an inner surface of the bag, a foam polyethylene sheet defining an outer surface of the bag and an absorbent core disposed therebetween.

The known urine-absorbent bag is disadvantageous in that the back layer necessarily has a relatively high rigidity due to the presence of these foam polyethylen and absorbent core. The urine-absorbent bag of such construction tends to be angularly bent, instead of being smoothly curved as the bag is put against the user's penis and such angularly bent location often leaves a gap between the bag and the user's penis through which a leakage of urine may occur.

SUMMARY OF THE INVENTION

Accordingly, it is a principal object of the invention to improve a fitness of the urine-absorbent bag around the user's penis.

The object set forth above is achieved, according to the invention, by a urine-absorbent bag having front and rear sections adapted to cover the user's penis, an opening for insertion of the penis into the bag and a bottom opposed to the opening, one of the front and rear sections comprises a liquid-permeable inner sheet, a liquid-impermeable outer sheet and a liquid-absorbent core disposed therebetween, wherein the liquid-absorbent core is formed with grooves extending in predetermined directions and formed by locally thinning the core.

The grooves are preferably formed by locally compressing the absorbent core.

DESCRIPTION OF THE PREFERRED EMBODIMENT

Figure 1:
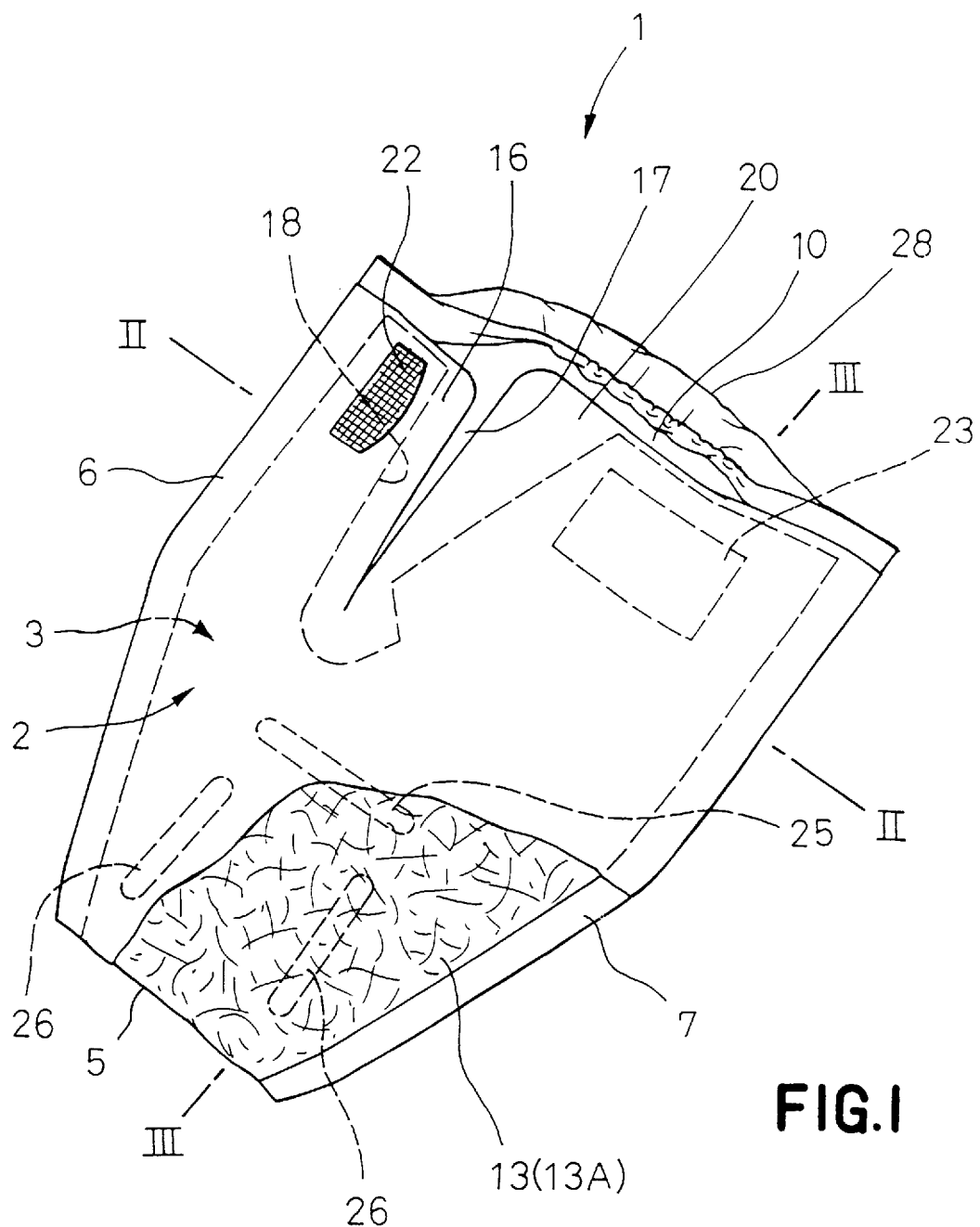
FIG. 1 is a perspective view exemplarily showing a urine-absorbent bag according to the invention as partially broken away.
Figure 2:
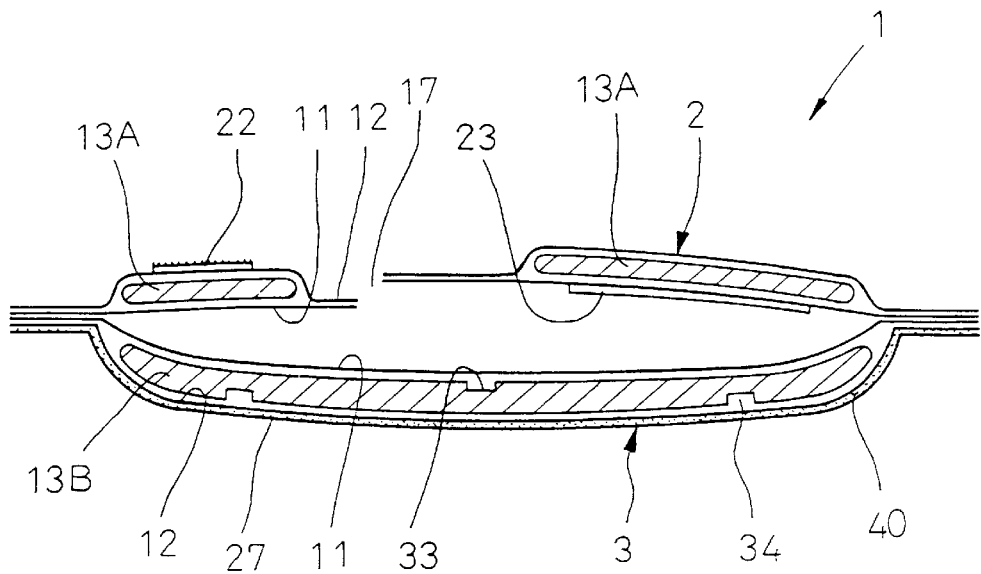
FIG. 2 is a sectional view taken along line II—II in FIG. 1.
Figure 3:
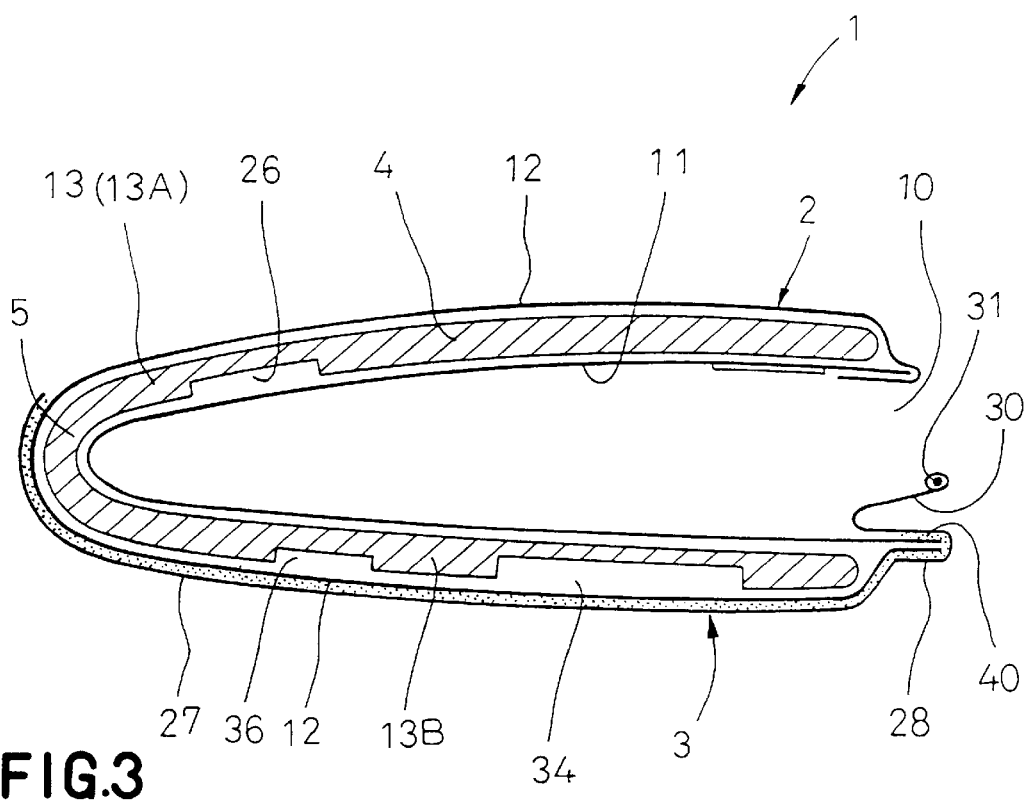
FIG. 3 is a sectional view taken along line III—III in FIG. 1.

A urine-absorbent bag 1 shown by FIGS. 1, 2 and 3 in a perspective view as partially broken away, in a sectional view taken along line II—II and in a sectional view taken along line III—III comprises a front section 2 and a rear section 3. In use of the urine-absorbent bag 1, the user's penis is inserted thereinto with the front section 2 facing outward and the rear section 3 facing the user's body. The front and rear sections 2, 3 are continuous with each other along a bottom edge 5 of the bag 1, overlap each other and bonded together along transversely opposite side edges 6, 7 of the bag 1, leaving a top edge not bonded together so as to define and opening 10. Each of these front and rear section 2, 3 comprises a liquid-permeable inner sheet 11, a liquid-impermeable outer sheet 12 and a liquid-absorbent core 13 disposed therebetween. These inner sheet 11 and outer sheet 12 are bonded together along portions thereof extending beyond a peripheral edge of the core 13. The respective inner sheets 11 of the front and rear sections 2, 3 are bonded together along the side edges 6, 7 of the bag 1. It should be understood that, of the core 13 continuously extending across the front and rear sections 2, 3, a portion occupying the front section 2 is designated by reference numeral 13A and a portion occupying the rear section 3 is designated by reference numeral 13 B. It should be also understood that both the front and rear sections 2, 3 and the sheets 11, 12 are illustrated as if they are slightly spaced from each other along their mutually bonded regions in order to avoid an indistinctness. The line III—III in FIG. 1 lies a little to the right hand with respect to a center line transversely of the bag 1.

The front section 2 has a notch 17 extending downward from an edge 16 of the opening 10 so as to divide an upper portion of the fron section 2 into right and left regions. On both sides of this notch 17, the inner sheet 11 and the outer sheet 12 are bonded together along portions thereof extending beyond a generally V-shaped notch 18 of the core 13A. A flap-like portion formed on the right side of the notch 17 as viewed in FIG. 1 by the inner sheet 11 and the outer sheet 12 bonded together along marginal regions thereof extending beyond the V-shaped notch 18 of the core 13A serves as a tab 20 used to put the urine-absorbent bag 1 against the user's penis. On the left side of the notch 17, a hook member 22 of a mechanical fastening system known under the trade mark "Velcro" is attached to an outer surface of the outer sheet 12 and on the right side of the notch 17, a loop member 23 of the mechanical fastening system is attached to an inner surface of the inner sheet 11. An inner surface of the core 13A in the front section 2 is symmetrically formed in the proximity of the bottom edge 5 with a transversely extending first groove 25 and a longitudinally but slight obliquely extending pair of second grooves 26.

The rear section 3 has a nonwoven fabric 27 integrally laminated by hot melt type adhesive 40 to the outer surface of the outer sheet 12. This nonwoven fabric 27 is folded back along an edge 28 of the opening 10 in a general Z-shape (in an inverted general Z-shape as viewed in FIG. 3) and partially bonded by adhesive 40 to the inner sheet 11 so that a forward end of this folded portion may extend form an inner side to an outer side of the bag 1 to define a free end 30. An elastic member 31 is secured in a elastically stretched condition to this free end 30 parallel to the edge 28 of the opening 10. Such free end 30 has transversely opposite ends thereof disposed between the respective inner sheets 11 of the front and rear sections 2, 3 overlapping along the side edges 6, 7 of the bag 1 and bonded to these inner sheets 11. Between the transversely opposite side edges 6, 7 of the bag 1, the free end 30 functions as a dam to block a leakage of urine as will be described in more detail. The core 13B occupying the rear section 3 has third to seventh grooves 33–37 on inner and outer surfaces of the core 13B arranged in a layout illustrated by FIG. 4.

Figure 4:
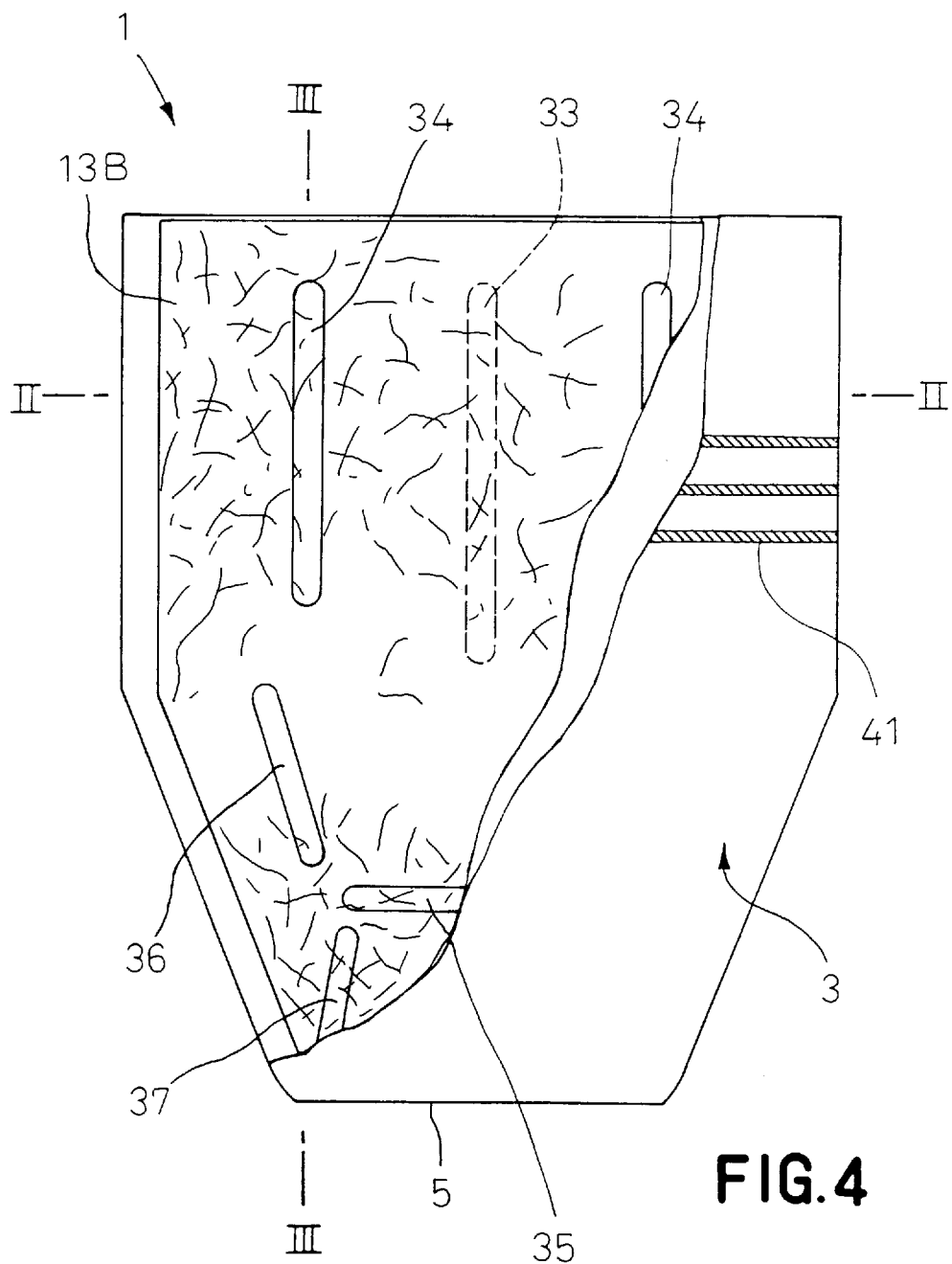
FIG. 4 is a fragmentary plan view showing a rear section of the urine-absorbent bag as partially broken away.

In the rear section 3 of the urine-absorbent bag 1 shown by FIG. 4 in a plan view as partially broken away, the liquid-absorbent core 13B occupying this rear section 3 has the third groove 33 (indicated by a broken line) formed in an upper region of the core 13B on an inner surface of the core 13B so as to extend in a vertical direction of the core 13B substantially across a transversely middle region of the core 13B, a pair of the fourth grooves 34 (each indicated by a solid line) formed in the upper region of the core 13B on the outer surface of the core 13B so as to lie on transversely opposite sides with the third groove 33 between and to extend in a vertical direction of the 13B, the fifth groove 35 formed in a lower region of the core 13B on the outer surface of the core 13B so as to extend transversely of the core 13B and the sixth and seventh grooves 36, 37 (each indicated by a solid line) formed in a lower region of the core 13B on the outer surface of the core 13B so as to extend substantially in vertical but somewhat oblique directions of the core 13B.

The manner in which the bag 1 of such arrangement is used will be described. After insertion of the user's penis into the bag 1, the loop member 23 is anchored to the hook member 22 of the mechanical fastening system so as to put the opening 10 of the bag 1 closely around the user's penis with the tab 20 of the front section 2 held by the user's fingers. With the bag put on the user in this manner, right and left flap-like portions defining the notch 17 therebetween may be overlapped one upon another to put the opening edge 16 of the front section 2 against the user's penis from the outer side and the presence of the third and fourth grooves 33, 34 extending on the core 13B in the vertical direction allows the opening edge 28 of the rear section 3 to be smoothly curved and thereby to be put against the user's penis from the inner side. The third groove 33 formed on the inner surface of the core 13B facilitates the core 13B to be deformed in an outwardly convex shape while the fourth groove 34 formed on the outer surface of the core 13B facilitates the core 13B to be deformed in an inwardly convex shape. The respective edges 16, 28 defining the opening 10 properly fit the user's penis from inner and outer sides thereof, leaving no gap between the user's penis and the bag 1 which might cause a leakage of urine.

The known urine-absorbent bag has been disadvantageous in that the bag of excessively large size with respect to the user's penis readily generates wrinkles or folds which may cause a leakage of urine even if the core 13 is provided with the grooves. On the contrary, the bag 1 according to the invention reliably eliminates an apprehension of such leakage because the invention allows the free edge 30 to fit the user's penis and thereby to function as a leakage blocking dam.

In the urine-absorbent bag 1, there are provided adjacent a common bottom edge 5 of the core 13A, 13B the grooves 25 and 35 extending transversely of the bag 1 and the grooves 26, 36, 37 extending in the vertical but somewhat oblique directions. These grooves facilitates the common bottom of the core 13A, 13B to be deformed following the glans of the inserted penis.

According to the invention, the core 13 is formed with those grooves in order to improve a fitness of the urine-absorbent bag 1 to the user's penis and to facilitate the bag 1 to be deformed in conformity with a shape of the user's penis. Therefore, various factors such as the number, the positions, the orientations, the width and the lengths of the respective grooves may be selected depending on the particular condition under which the bag 1 is used. However, the core 13 preferably has at least the groove 33 centrally formed on the inner surface of the core 13B and extending in the vertical direction because this groove 33 assures a reliable fitness of the bag 1 to the user's penis at the opening 10.

Liquid-permeable nonwoven fabric or perforated plastic film may be used a material for the inner sheet of the bag 1 and plastic film, more preferably air-permeable but liquid-impermeable plastic film may be used as material for the outer sheet 12 of the bag 1.

Fluff pulp or a mixture of 40–100 w % fluff pulp and 60–0 w % superabsorptive polymer particles may be used as material for the liquid-absorbent core 13. 20 or less w % thermoplastic synthetic fibers may be mixed into such material so that the grooves of the core 13 may be easily formed and/or a strength of the core 13 may be increased.

While the outer side of the rear section 3 is covered with the nonwoven fabric 27 so that the rear section 3 may offer a soft touch when the rear section 3 comes in contact with the user's skin, such outer covering may be eliminated if it is unnecessary. When the leakage blocking dam is formed by the free end 30 of the nonwoven fabric 27, the free end 30 is preferably provided with water-repellency or liquid-impermeability. Appropriate pattern 41 (See FIG. 4) may be printed on the nonwoven fabric 27 if it is desired to facilitate front and rear sides of the bag 1 to be identified.

The grooves 25, 26, 33–37 on the core 13 may be obtained by subjecting the core 13 to debossing or heat debossing. The grooves formed in this manner have a fiber density higher in bottoms thereof than the remaining portions and spreading of urine in the bottoms occurring longitudinally of the grooves will be promoted. In a consequence, the urine-absorbent bag 1 according to the invention allows a liquid absorbing capacity of the core 13 to be fully utilized. To bond the respective components one to another may be achieved by using adhesive agents such as hot melt type adhesive or the heat-sealing technique so far as the components to be bonded are of heat-sealable nature.

While the front section 2 is continuous with the rear section 3 and have a common bottom edge 5 in the urine-bag 1 illustrated, an alternative arrangement is also possible in which the front section 2 and the rear section 3 are separately provided. In any way, it is possible to dispose the liquid-absorbent core 13 in only one of these front and rear sections 2, 3. In addition, it is also possible to construct the urine-absorbent bag 1 in which the opening 10 includes no leakage blocking dam. Furthermore, the leakage blocking dam may be formed also by a member other than the nonwoven fabric 27, for example, liquid-impermeable plastic film bonded to the opening 10.

The invention solves the problems such that the wrinkles and/or the folds appearing in the bag when it is put on the user's penis have often caused a leakage of urine along these wrinkles and folds, since the urine-absorbent bag according to the invention has the grooves formed on the liquid-absorbent core so arranged that the bag may be smoothly deformed following a shape of the penis without significant wrinkles and/or angular folds. Specifically, the grooves extending from the top toward the bottom of the bag allow the peripheral edge of the opening to fit around the user's penis and improves a leakage blocking effect. The grooves formed so as to have a fiber density higher in the bottoms thereof than the region around them contribute to promote the urine spread along the bottoms longitudinally of these grooves and thereby allow the liquid absorbing capacity of the liquid-absorbent core to be fully utilized.

Though not shown, the bag 1 is generally used together with a known integral disposable diaper or incontinence pants.

What is claimed is:

1. A urine-absorbent bag comprising:
   a laminate including:
      a liquid-permeable inner sheet, a liquid-impermeable outer sheet, and a liquid-absorbent core disposed between said inner sheet and said outer sheet;

said laminate defining a front section, a rear section, an opening for insertion of the user's penis into said bag, and a bottom opposed to said opening;

said front section being provided with a generally V-shaped notch extending form an edge of said opening toward said bottom so as to divide an upper portion of said fron section into two opposite regions respectively forming a flap along opposing edges of said notch, and fastening members respectively disposed on said opposite regions and being fastenable together to overlap the flaps on each other and against the user's penis; and a plurality of grooves disposed in said core, said grooves extending in predetermined directions and formed by locally thinning said core.

2. The urine-absorbent bag according to claim 1, wherein the said grooves are formed by locally compressing the core.

3. The urine-absorbent bag according to claim 1, wherein the liquid-absorbent core contains superabsorptive polymer particles of at least 30% by weight and each groove has a fiber density higher in a bottom thereof than in a region around the bottom.

4. The urine-absorbent bag according to claim 1, wherein the grooves extend from the opening of the bag toward the bottom thereof.

5. The urine-absorbent bag according to claim 1, wherein the grooves comprise a set of grooves extending from the opening toward the bottom of the bag and grooves extending transversely of the first-mentioned grooves.

6. The urine-absorbent bag according to claim 1, wherein the grooves are formed on a inner surface of the liquid-absorbent core.

7. The urine-absorbent bag according to claim 1, wherein the grooves are formed on an outer surface of the liquid-absorbent core.

8. The urine-absorbent bag according to claim 1, wherein the grooves are formed on the inner surface as well as on the outer surface of the liquid-absorbent core.

* * * * *